(12) United States Patent
Marik

(10) Patent No.: US 7,645,281 B2
(45) Date of Patent: Jan. 12, 2010

(54) ANATOMIC IMPLANTS DESIGNED TO MINIMIZE INSTRUMENTS AND SURGICAL TECHNIQUES

(75) Inventor: Greg Marik, Germantown, TN (US)

(73) Assignee: Warsaw Orthopedic, Inc.

( * ) Notice: Subject to any disclaimer, the term of this patent is extended or adjusted under 35 U.S.C. 154(b) by 0 days.

(21) Appl. No.: 11/932,221

(22) Filed: Oct. 31, 2007

(65) Prior Publication Data
US 2008/0051907 A1 Feb. 28, 2008

Related U.S. Application Data

(62) Division of application No. 10/768,420, filed on Jan. 30, 2004, now abandoned.

(51) Int. Cl.
  *A61F 2/46* (2006.01)
  *A61B 17/00* (2006.01)
(52) U.S. Cl. ............... 606/99; 606/79; 623/17.15; 623/17.16
(58) Field of Classification Search ... 623/17.11–17.16; 606/79–80, 99
See application file for complete search history.

(56) References Cited

U.S. PATENT DOCUMENTS

| | | |
|---|---|---|
| 4,714,469 A | 12/1987 | Kenna |
| 5,306,307 A | 4/1994 | Senter et al. |
| 5,330,481 A | 7/1994 | Hood et al. |
| 5,352,230 A | 10/1994 | Hood |
| 5,383,242 A | 1/1995 | Bigler et al. |
| 5,609,635 A | 3/1997 | Michelson |
| 5,674,296 A | 10/1997 | Bryan et al. |
| 5,797,917 A | 8/1998 | Boyd et al. |
| 6,083,228 A | 7/2000 | Michelson |
| 6,258,125 B1 | 7/2001 | Paul et al. |
| 6,277,149 B1 | 8/2001 | Boyle et al. |
| 6,425,920 B1 | 7/2002 | Hamada |
| 6,440,139 B2 | 8/2002 | Michelson |
| 6,447,547 B1 | 9/2002 | Michelson |
| 6,482,209 B1 | 11/2002 | Engh et al. |
| 6,503,279 B1 | 1/2003 | Webb et al. |
| 6,517,544 B1 | 2/2003 | Michelson |
| 6,554,863 B2 | 4/2003 | Paul et al. |

(Continued)

FOREIGN PATENT DOCUMENTS

WO    9963891    12/1999

OTHER PUBLICATIONS

T. Hoogland et al., "Total Lumbar Intervertebral Disc Replacement: Testing of a New Articulating Spacer in Human Cadaver Spines," 24th Annual ORS, Feb. 21-23, 1978, p. 102, Dallas, Texas.

(Continued)

*Primary Examiner*—Eduardo C Robert
*Assistant Examiner*—Mary Hoffman

(57) ABSTRACT

A method of implanting a vertebral implant in a void between a pair of vertebral endplates comprises positioning the vertebral implant between the vertebral endplates and coupling an implantation tool to the vertebral implant. The method further comprises actuating the implantation tool to generate alternating motion relative to the vertebral endplates. The alternating motion has a speed and creates a displacement of the vertebral implant. The method further comprises seating the vertebral implant into a profile formed in at least one of the vertebral endplates and decoupling the implantation tool from the vertebral implant. The vertebral implant remains implanted in the at least one vertebral endplate.

16 Claims, 3 Drawing Sheets

U.S. PATENT DOCUMENTS

| | | |
|---|---|---|
| 6,610,066 B2 | 8/2003 | Dinger et al. |
| 6,695,851 B2 * | 2/2004 | Zdeblick et al. ............... 606/96 |
| 7,270,679 B2 * | 9/2007 | Istephanous et al. ..... 623/17.11 |
| 2002/0026242 A1 | 2/2002 | Boyle et al. |
| 2002/0062153 A1 | 5/2002 | Paul et al. |
| 2002/0128715 A1 | 9/2002 | Bryan et al. |
| 2003/0009224 A1 | 1/2003 | Kuras |
| 2003/0036798 A1 | 2/2003 | Alfaro et al. |
| 2003/0069642 A1 | 4/2003 | Ralph et al. |
| 2003/0074076 A1 | 4/2003 | Ferree et al. |
| 2003/0078666 A1 | 4/2003 | Ralph et al. |
| 2003/0083748 A1 | 5/2003 | Lee et al. |

OTHER PUBLICATIONS

European Patent Office, PCT International Searching Authority, "Notification of Transmittal of The International Search Report and The Written Opinion of the International Searching Authority, or the Declaration," May 4, 2005, 15 pages.

* cited by examiner

ANATOMIC IMPLANTS DESIGNED TO MINIMIZE INSTRUMENTS AND SURGICAL TECHNIQUES

CROSS-REFERENCE

This application is a divisional of U.S. patent application Ser. No. 10/768,420, filed Jan. 30, 2004, and is hereby incorporated by reference in its entirety.

BACKGROUND

In the treatment of diseases, injuries or malformations affecting spinal movement and disc tissue, it has long been common practice to remove a portion or all of a degenerated, ruptured, or otherwise failing disc. Following the loss or removal of disc tissue, intervertebral devices have been implanted between the remaining vertebrae to promote fusion or to restore motion to the treated area of the spine. To properly seat the implant, conventional methods of implantation often require the use of complex measurement and instrumentation systems for preparing the bone to match the implant. A mismatch between the implant and the prepared bone can cause an improper seating of the implant. Therefore, a method and apparatus are needed which simplify the instrumentation required for implantation and improve the fit between the implant and the adjacent vertebrae.

SUMMARY

This disclosure relates to a new method for implanting an intervertebral implant in a void between a pair of vertebral endplates. In one embodiment, a method of implanting a vertebral implant in a void between a pair of vertebral endplates comprises positioning the vertebral implant between the vertebral endplates and coupling an implantation tool to the vertebral implant. The method further comprises actuating the implantation tool to generate alternating motion relative to the vertebral endplates. The alternating motion has a speed and creates a displacement of the vertebral implant. The method further comprises seating the vertebral implant into a profile formed in at least one of the vertebral endplates and decoupling the implantation tool from the vertebral implant. The vertebral implant remains implanted in the at least one vertebral endplate.

In another embodiment, a method of treatment comprises accessing a disc space between a pair of vertebral endplates and coupling an implantation tool to an intervertebral implant. The method further comprises positioning the intervertebral implant in the disc space between the vertebral endplates, actuating the implantation tool to generate an alternating motion in the intervertebral implant, and abrading the vertebral endplates adjacent to the intervertebral implant with the intervertebral implant to create a seat in at least one of the vertebral endplates. The method further comprises decoupling the implantation tool from the intervertebral implant and depositing the intervertebral implant within the seat.

In still another embodiment, a method of treatment comprises accessing a disc space between a pair of vertebral endplates. The method further comprises attaching a first projection of an implantation tool to a first portion of a motion preserving implant and attaching a second projection of the implantation tool to a second portion of the motion preserving implant. The first portion of the motion preserving implant is movable with respect to the second portion. The method further comprises positioning the intervertebral implant in the disc space between the vertebral endplates, actuating the implantation tool to generate an alternating motion in the intervertebral implant, and abrading the vertebral endplates adjacent to the intervertebral implant with the intervertebral implant to create a seat in at least one of the vertebral endplates. The method further comprises removing the first and second projections from the motion preserving implant and depositing the intervertebral implant within the seat.

DETAILED DESCRIPTION

Figure 1:
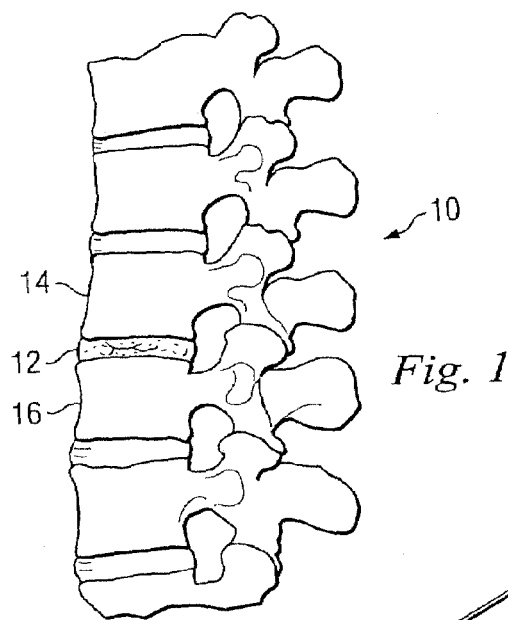
FIG. 1 is a side view of vertebral column having a destroyed disc.

The present disclosure relates generally to the field of orthopedic surgery, and more particularly to the instrumentation and techniques for inserting intervertebral devices. For the purposes of promoting an understanding of the principles of the invention, reference will now be made to embodiments or examples illustrated in the drawings, and specific language will be used to describe the same. It will nevertheless be understood that no limitation of the scope of the invention is thereby intended. Any alteration and further modifications in the described embodiments, and any further applications of the principles of the invention as described herein are contemplated as would normally occur to one skilled in the art to which the invention relates.

Referring first to FIG. 1, the numeral 10 refers to vertebral column with a damaged intervertebral disc 12 extending between vertebrae 14 and 16. In a typical surgical discectomy, the disc 12 is removed, creating a void between the two intact vertebrae 14 and 16. This procedure may be performed using an anterior, anterolateral, lateral, or other approach known to one skilled in the art. An implant according to an embodiment of the present invention may then be provided to fill the void between the two intact vertebrae 14 and 16. The embodiments of this disclosure may be generally directed toward articulating intervertebral prostheses which restore at least some range of motion at the site of the removed disc 12. It is understood, however, that in alternate embodiments, the methods and apparatus of this disclosure may be used to implant non-articulating devices which may promote fusion of the vertebrae 14 and 16. Furthermore, although the embodiments to be described are premised upon the removal of a single disc, it is understood that the methods and apparatus of the invention may be applied to the insertion of a vertebral body replacement device between two vertebrae following a corpectomy, in which at least one vertebral body has been removed.

Figure 2:
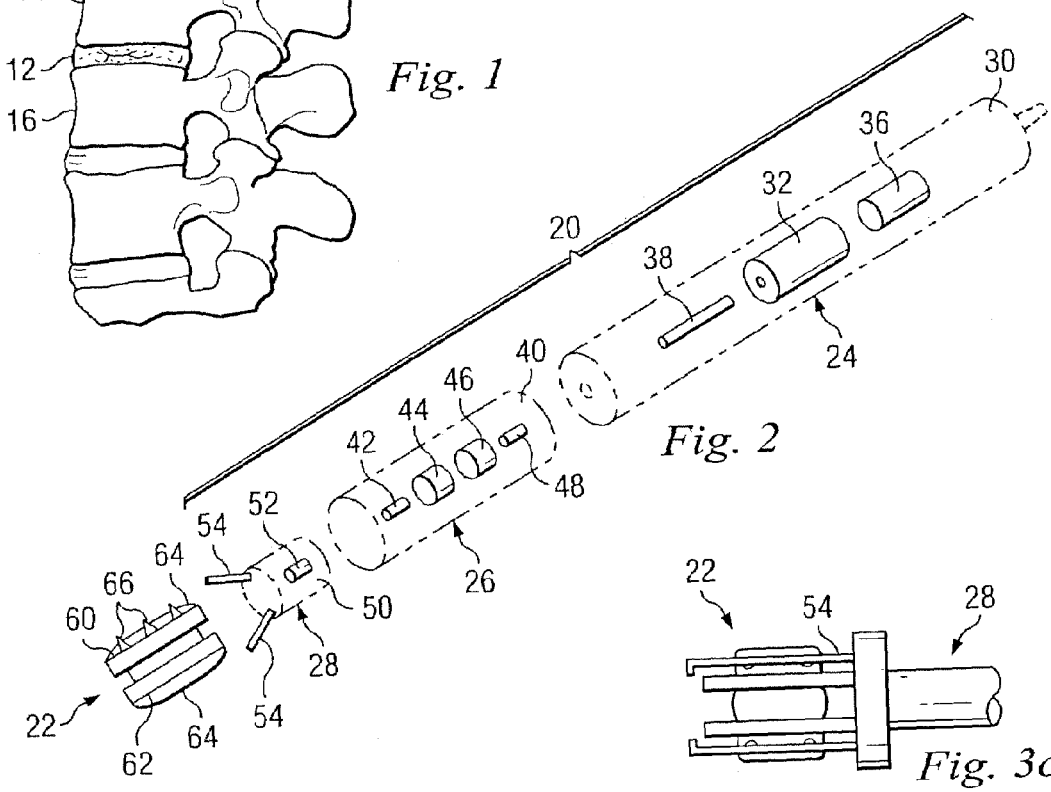
FIG. 2 is a exploded schematic view of an apparatus for installing an intervertebral device.
Figure 3C:
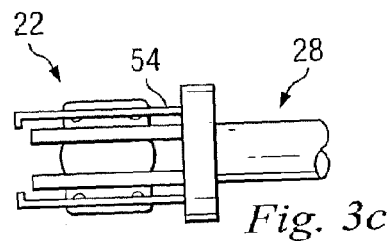
Figure 3A:
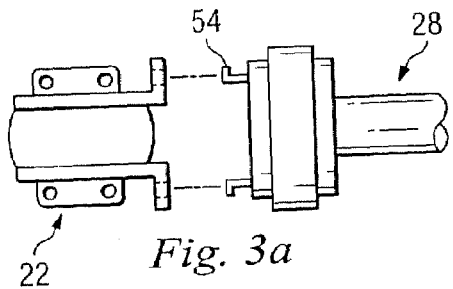
Figure 3D:
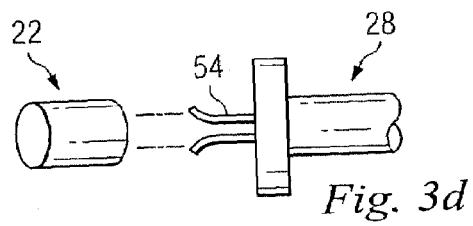
Figure 3B:
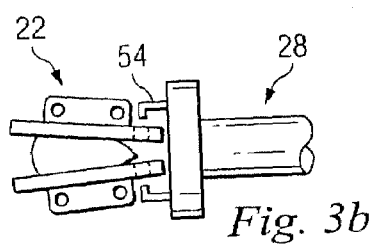
Figure 3E:
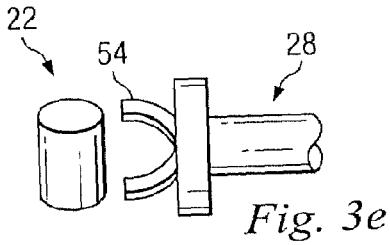

Referring now to FIG. 2, an implantation tool 20 for inserting an implant 22 between two vertebrae 14, 16 (of FIG. 1) may include a handpiece 24, a coupling mechanism 26, and an implant adapter 28.

In the embodiment of FIG. 2, the handpiece 24 may include a handpiece body 30 for housing a power device 32, such as an electric motor, coupled to an electrical power connector 36 for driving a drive shaft 38. Although this embodiment describes an electrically powered apparatus, it is understood that alternative power devices may be selected including pneumatic, battery, or gas powered devices. These alternative power devices may be supported by additional or alternative components.

The coupling mechanism 26 may be provided to convert and control, if needed, the motion from the power device 32 into a vibratory, reciprocating, oscillatory, or other type of direction alternating movement. The coupling mechanism 26 may include a body 40 for housing a drive mechanism 42 for transferring output motion to the implant adapter 28. The drive mechanism 42 may be connected to a conversion mechanism 44, such as one or more cams, for creating reciprocating motion. The coupling mechanism 26 may further include a reduction mechanism 46, such as a gearbox connected to the conversion mechanism 44 and/or the drive mechanism 42, for selectively altering the speed and/or force transmitted by the drive mechanism 42. The coupling mechanism 26 may also include a drive mechanism 48 for transmitting motion from the handpiece 24. The coupling mechanism 26 may include additional or alternative mechanisms as may be necessary to convert and control the motion from the power device 32 into a desired output motion. U.S. Pat. No. 6,610,066, which is incorporated by reference herein, discloses a reciprocating surgical tool having components for converting rotary motion of a powered handpiece into reciprocating motion.

Figure 3F:
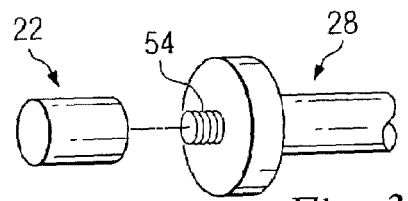
FIGS. 3a-3f are exemplary implant adapters configured for a variety of intervertebral implants.

The implant adapter 28 may include a housing 50 and a drive adapter 52 for removably connecting the implant adapter 28 to the coupling mechanism 26. The implant adapter 28 may further include an implant engagement mechanism 54 for engaging the implant 22. The implant engagement mechanism 54 may be configured to engage a particular implant 22 or may be adjustable to permit engagement with a variety of implants. FIGS. 3a-3f illustrate exemplary embodiments of the implant adapter 28 configured to mate with a variety of implant devices 22. The engagement mechanisms 54 can be hooks (FIG. 3a, 3d), pins (FIG. 3b), clamps (FIG. 3c), gripping arms (FIG. 3e), or a threaded projection (FIG. 3f). This list is not exhaustive, and other mechanisms may be used for attaching an implant 22 to the implant adapter 28.

The components of the implantation tool 20 may be made of durable, medically acceptable materials, such as stainless steel, hard coated anodized aluminum, or titanium, for example, capable of being sterilized to medical standards, such as by steam or flash autoclaving, gas sterilization, and/or soaking in a disinfectant solution. Accordingly, the implantation tool 20 may be designed for repeated use. The shape, size, and configuration of the components 24-54 are merely exemplary and any of a variety of alternative configurations may be desirable.

The implant 22 may be a prosthesis such as is disclosed in U.S. Pat. No. 6,540,785; U.S. patent application Ser. No. 10/303,569; or U.S. patent application Ser. No. 10/042,589 which are incorporated herein by reference. However, as previously stated, other articulating and non-articulating implant 22 designs, including fusion promoting devices, may be installed using the implantation tool 20. The implant 22 may have a surfaces 60 and 62 having a rough coating 64, features 66 and/or other surface textures for abrading the endplates of the adjacent vertebrae in preparation for seating the implant. For example, a coating 64 of biocompatible and osteoconductive material such as nonspherical sintered beads or hydroxyapatite may cover all or a portion of the surfaces 60 and 62. Other suitable coatings 64 or treatments may include a porous bead coating, a porous mesh coating, osteogenic peptide coating, growth factor coating, rh-BMP coating, and/or grit blasting. Suitable features 66 may include spikes (as shown in FIG. 2), serrations, ridges, fins, pyramidal projections, and/or other surface textures.

The implantation tool 20 may be assembled by attaching the handpiece 24 to the coupling mechanism 26, specifically, the drive shaft 38 may engage the drive mechanism 48. The implant adapter 28 may be attached to the coupling mechanism 26, specifically, the drive mechanism 42 may engage the drive adapter 52. The electrical power connector 36 may be connected to a power source (not shown) such as an electrical outlet. The implant 22 may be attached to the engagement mechanism 54.

The components 24, 26, 28 of the implantation tool 20 may be modular, permitting an implantation tool 20 to be assembled and tailored for a particular application. For example, to achieve a desired type of motion or a desired displacement in the implant adapter 28, a coupling mechanism 26 may be selected having a conversion mechanism 40 designed to generate the desired motion. Likewise, to adapt to a particular implant 22, an implant adapter 28 may be selected having an engagement mechanism 54 suitable for engaging the implant 22. In some embodiments, the design of the handpiece 24, the coupling mechanism 26, and/or the implant adapter 28 may combine or eliminate components. For example, drive shaft 38 may directly engage the conversion mechanism 44 or the reduction mechanism 46 without requiring a drive mechanism 48.

In preparation for installing the implant 22, a decompression procedure may be performed by removing the diseased or damaged disc 12. The space vacated by the disc 12 may be distracted to receive the implant 22. The implant 22 may be placed into the space between the vertebrae 14 and 16. Power may be supplied to the power device 32 by the power connector 36 to rotably drive the drive shaft 38. The drive shaft 38, in turn, may drive the drive mechanism 48 of the coupling mechanism 26. The rotary output of the handpiece 24 may pass through the reduction mechanism 46 of the coupling mechanism 26 to reduce the speed, increase force, or change direction of the rotary motion. The rotary motion may be converted to a selected vibratory, reciprocating, oscillatory, pulsating or other alternating movement by the conversion mechanism 44 of the coupling mechanism 26. The selected alternating movement may be transmitted by the conversion mechanism 44, through the coupled drive mechanism 42 and drive adapter 52, to vibrate the implant adapter 28.

The vibration of the implant adapter 28 may, in turn, cause the implant 22 to vibrate or otherwise generate an alternating movement relative to the adjacent bone of the vertebral endplates. The vibration may cause the rough or featured surfaces 60, 62 of the implant 22 to abrade the adjacent bone, creating an impression of the contour and features of the surfaces 60 and 62 in the vertebral endplates. Thus, the implant 22 may be the master pattern for its own implantation seat, allowing the general geometry of the host bone to be duplicated and the normal anatomy generally matched, and thereby potentially creating a better fit between the implant 22 and the vertebrae 14, 16. After the implant 22 is seated in the adjacent bone of the vertebral endplates, the implant 22 may be decoupled from the implant adapter 28 by releasing the engagement mechanism 54 from the implant 22. After the decoupling, the implant 22 may be securely installed between the vertebral bodies 14, 16.

This technique may also reduce the need for complex fixtures, milling instrumentation, and measurement devices such as trials. Correspondingly, the surgical access area may be smaller than is required with more complex rigging. The surgical preparation needed may also be reduced.

Given that most vertebral endplates are typically not flat, but instead have a convex superior endplate and a concave inferior endplate, the self seating action described above may permit an implantation that is uniquely suited to the particular patient's spine, thus promoting long term stability. To further promote the long term stability of the implant 22, the abrading action may releases bone particles which may be redeposited in the area of the implant 22 to stimulate bone ingrowth.

As shown in FIGS. 4-8, a relative alternating movement 70, provided by the implant adapter 28 (not shown) for seating the implant 22, may be a vibration which moves the implant 22 generally back and forth along a longitudinal axis 72 which extends through the vertebral bodies 14, 16.

Figure 4:
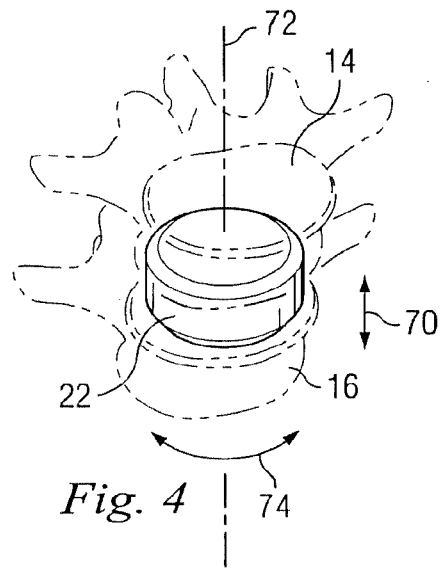
FIGS. 4-10 are perspective views of a vertebral implant between a pair of vertebral bodies according to embodiments of the current disclosure.

Referring to FIG. 4, in addition to or alternative to the movement 70, a relative movement 74 may reciprocally rotate the implant 22 about the longitudinal axis 72.

Figure 5:
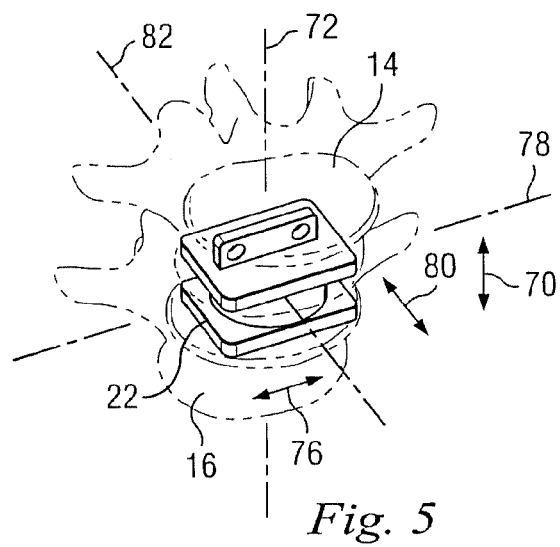

Referring to FIG. 5, a relative movement 76 may also or alternatively vibrate the implant 22 along an axis 78 which extends from the anterior side of the implant through the disc space to the posterior side of the implant. A relative motion 80 may also or alternatively vibrate the implant 22 along an axis 82 which extends transversely through the disc space. The transverse motion 80, in this embodiment, may be particularly suited to an implant 22 having a projection 66, such as the fin of FIG. 5, which extends in the anterior-posterior direction 78. Vibrating the implant 22 in a direction opposite of the anterior direction of implantation may help to prevent the implant from ejecting after implantation.

Figure 6:
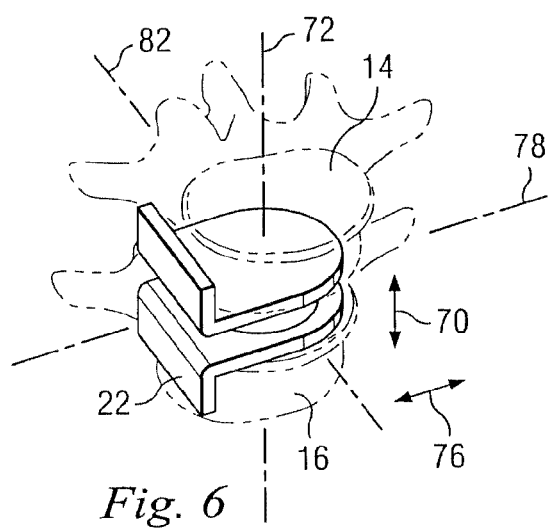

Referring now to FIG. 6, in an embodiments where the implant 22 is configured to contact a side portion of the adjacent vertebrae 14, 16, the relative motions 70, 76 may also abrade a side portion of the adjacent vertebrae 14, 16 as the implant is seated.

Figure 7:
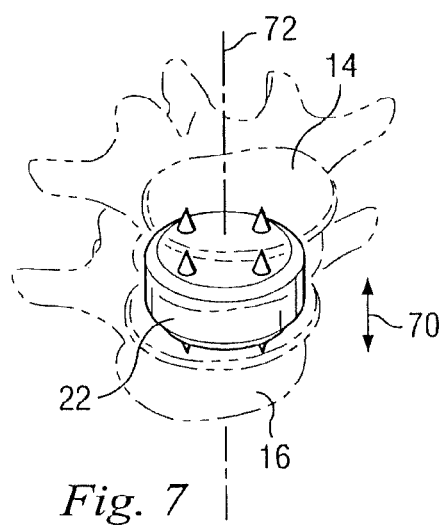

Referring now to FIG. 7, in an embodiment where the implant 22 includes a plurality of elongated spikes, the relative motion 70 in the direction of the longitudinal axis 72 may be appropriate to drive the spikes into the adjacent vertebrae 14, 16.

Figure 8:
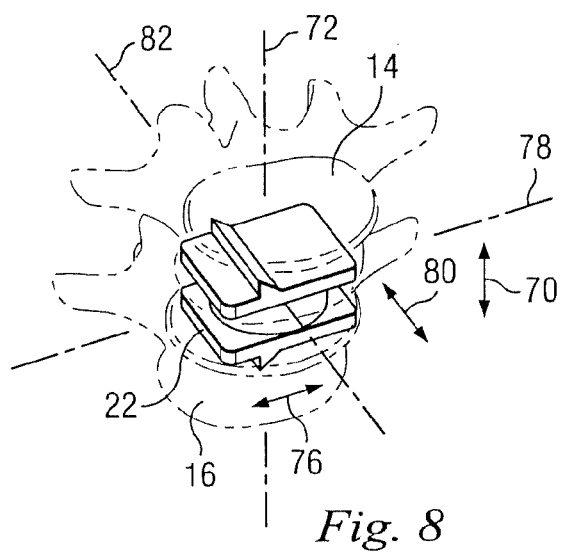

Referring now to FIG. 8, the relative movement 76 may also or alternatively vibrate the implant 22 along the anterior-posterior axis 78. The relative motion 80 may also or alternatively vibrate the implant 22 along the transverse axis 82. The transverse motion 80, in this embodiment, may also be particularly suited to an implant 22 having a transverse projection 66, such as the fin of FIG. 8. Vibrating the implant 22 in a direction opposite of the anterior direction of implantation may help to prevent the implant from ejecting after implantation.

Figure 9:
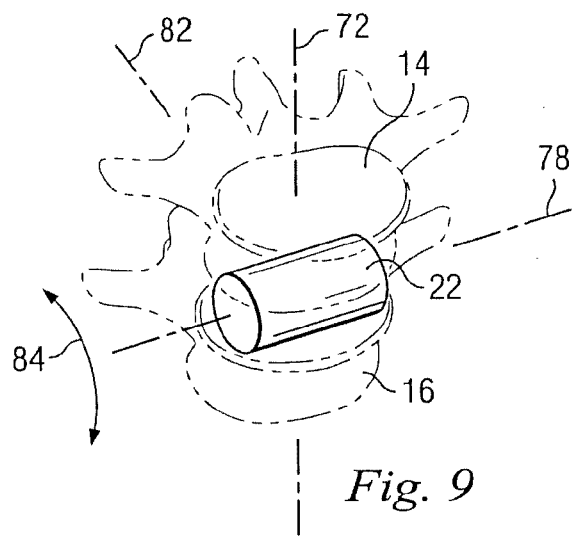

Referring now to FIG. 9, in an embodiment where the implant 22 is generally cylindrical and implanted along the axis 78, a relative motion 84 may reciprocally rotate the implant 22 about the axis 78.

Figure 10:
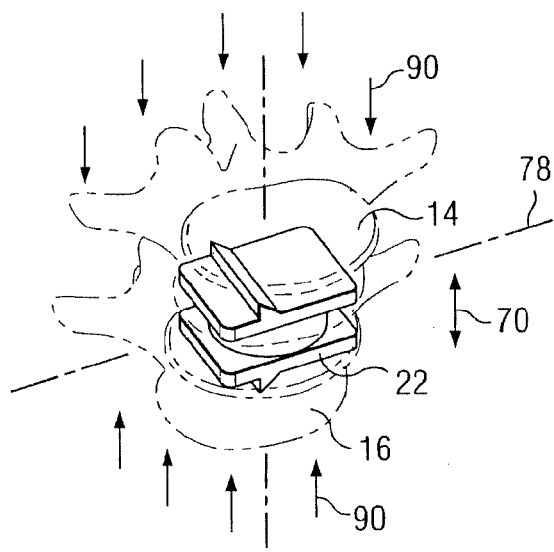

In one embodiment, as shown in FIG. 10, a force 90 may be applied to draw the vertebrae 14, 16 together while the vibration motion 70 is delivered in the longitudinal direction 72. The force 90 may push the endplates together (as shown) or may, alternatively, pull the endplates together. The combination of force 90 and vibration motion 70 may enhance the seat of the implant 22.

It is understood that the relative movements 70, 74, 76, 80, 84 are merely exemplary and other relative motions, such as arc shaped motions, multi-directional, or random motions, may be selected based upon the spinal location, implant configuration, surgical approach or surgical application. The speed, force, and other characteristics of the movement of the implant 22 may be adjusted, for example, by varying the speed of the power device 34 or components of the reduction mechanism 46.

Other characteristics of the movement of the implant 22 such as the displacement distance, may be controlled by, for example, the conversion mechanism 44. In one embodiment, for example, a cam may be designed to provide a stroke of 2-3 millimeters in the implant 22. The displacement of implant 22 may also be managed by controlling the magnitude of the vibration, oscillation, or other alternating movement. The displacement of the implant caused by the alternating movement 70, 74, 76, 80, 84 may be, for example 2 to 3 millimeters, however larger or smaller displacements may be appropriate for certain applications.

The speed/ frequency of the movements 70, 74, 76, 80, 84, the compressive force 90 and the displacement of the implant 22 may be varied as the implant 22 is embedded in the vertebral endplates. For example, greater speed, force, and displacement may be required to embed an elongated projection of the implant 22, however as that projection becomes embedded and the profile of the implant 22 becomes less pronounced, the speed, force, and displacement may be reduced to seat the remainder of the implant 22. In some embodiments, software and circuitry (not shown) may be provided to the implantation tool 20 to control the movement implant 22 according to the profile of the implant 22, the hardness of the bone, the material of the coating 64, or other characteristics of the surgical application or components. In some embodiments, a dampener (not shown) may be included in the implantation tool 20 for dampening the vibration of the implant 22. The speed/ frequency of the movements 70, 74, 76, 80, 84 may also be selected to confine motion to the area of the implantation without creating micro motion of the whole spine.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means-plus-function clauses are intended to cover the structures described herein as performing the recited function and not only structural equivalents, but also equivalent structures.

What is claimed is:

1. A method of implanting a vertebral implant in a void between a pair of vertebral endplates, the method comprising:
   positioning the vertebral implant between the vertebral endplates, the vertebral implant having a surface feature formed thereon that aids in anchoring the implant to the vertebral endplates;
   coupling an implantation tool to the vertebral implant;
   actuating the implantation tool to generate alternating motion relative to the vertebral endplates, wherein the alternating motion has a speed and creates a displacement of the vertebral implant relative to the vertebral endplates to form a profile in the endplates substantially matching the profile of the implant, wherein actuating includes varying the speed of the alternating motion depending on the depth of the profile formed in the vertebral endplate;
   abrading the vertebral endplates adjacent to the intervertebral implant with the intervertebral implant to form the profile in the vertebral endplates;
   seating the vertebral implant into the profile formed in at least one of the vertebral endplates;

decoupling the implantation tool from the vertebral implant, wherein the vertebral implant remains implanted in the at least one vertebral endplate;

wherein the vertebral implant comprises a keel surface feature and the speed of the alternating motion is varied as the surface feature becomes seated in the at least one vertebral endplate.

2. The method of claim 1 further comprising embedding bone particles between the vertebral implant and the at least one vertebral endplate during the seating of the vertebral implant.

3. The method of claim 1 further comprising varying the displacement of the vertebral implant.

4. The method of claim 1 further comprising drawing the vertebral endplates toward each other while seating the vertebral implant.

5. The method of claim 1 wherein the displacement is 3 millimeters or smaller.

6. The method of claim 1 wherein the alternating motion is a vibration.

7. The method of claim 1 wherein the alternating motion is a rotating motion about a longitudinal axis extending through the vertebral endplates.

8. The method of claim 1 wherein the alternating motion is a rotating motion about an anterior-posterior axis extending through the void between the vertebral endplates.

9. A method of treatment comprising:

accessing a disc space between a pair of vertebral endplates;

coupling an implantation tool to an intervertebral implant;

positioning the intervertebral implant in the disc space between the vertebral endplates, the vertebral implant having a surface feature formed thereon that aids in anchoring the implant to the vertebral endplates;

actuating the implantation tool to generate an alternating motion in the intervertebral implant, wherein the alternating motion has a variable speed and creates a displacement of the vertebral implant relative to the vertebral endplates to form a seat in the endplates;

abrading the vertebral endplates adjacent to the intervertebral implant with the intervertebral implant to create the seat in at least one of the vertebral endplates, wherein abrading occurs by varying the speed of the alternating motion based on the hardness of the vertebral endplate;

decoupling the implantation tool from the intervertebral implant;

depositing the intervertebral implant within the seat; and wherein the intervertebral implant further includes a surface texture.

10. The method of claim 9 wherein the step of decoupling includes adjusting the implantation tool from a gripped position in which two projections extend into or around at least a portion of the intervertebral implant and an ungripped position in which the two projections are decoupled from the intervertebral implant.

11. The method of claim 9 wherein the intervertebral implant includes a surface contour and the step of abrading includes creating a first seat portion in the impression of the surface contour of the intervertebral implant.

12. The method of claim 11 wherein the intervertebral implant includes a projection extending from the surface contour and the step of abrading further includes creating a second seat portion in the impression of the projection.

13. The method of claim 9 wherein the alternating motion is a vibratory motion.

14. A method of treatment comprising:

accessing a disc space between a pair of vertebral endplates;

attaching a first projection of an implantation tool to a first portion of a motion preserving implant;

attaching a second projection of the implantation tool to a second portion of the motion preserving implant, wherein the first portion of the motion preserving implant is movable with respect to the second portion;

positioning the intervertebral implant in the disc space between the vertebral endplates, the vertebral implant having a surface feature formed thereon that aids in anchoring the implant to the vertebral endplates;

actuating the implantation tool to generate an alternating motion in the intervertebral implant wherein the alternating motion has a variable speed and creates a displacement of the vertebral implant relative to the vertebral endplates to form a seat in the endplates;

abrading the vertebral endplates adjacent to the intervertebral implant with the intervertebral implant to create the seat in at least one of the vertebral endplates, wherein abrading includes varying the speed of the alternating motion depending on the depth of the seat formed in the vertebral endplate;

removing the first and second projections from the motion preserving implant; and depositing the intervertebral implant within the seat.

15. The method of claim 14 wherein the step of attaching a first projection includes inserting the first projection into the first portion.

16. The method of claim 14 wherein the step of attaching a first projection includes extending the first projection around the first portion.

* * * * *